United States Patent [19]

Kariya et al.

[11] Patent Number: 4,694,095
[45] Date of Patent: Sep. 15, 1987

[54] PHOSPHORIC ACID DITHIOESTERS, AND INSECTICIDES CONTAINING SAID DITHIOESTERS

[75] Inventors: Akinori Kariya, Higashi Murayama; Shukichi Nabekawa, Tokyo; Yoshifusa Hara, Tokyo; Junji Taguchi, Tokyo, all of Japan

[73] Assignees: Hironori Kushibiki; Nippon Chemical Industrial Co., Ltd., both of Tokyo, Japan

[21] Appl. No.: 894,646

[22] Filed: Aug. 8, 1986

[51] Int. Cl.$^4$ ................. A01N 57/02; C07F 9/165
[52] U.S. Cl. .................................................. 558/186
[58] Field of Search ................. 558/186; 514/127, 128

[56] References Cited

FOREIGN PATENT DOCUMENTS 767000  5/1970  Belgium .............................. 514/127

Primary Examiner—Anton H. Sutto
Attorney, Agent, or Firm—Tilton, Fallon, Lungmus & Chestnut

[57] ABSTRACT

An organo phosphoric acid dithioester is produced by reacting either O-ethyl.S-normalpropyldithiophosphoric acid salt and substituted ethylmercaptoethyl halide or O-ethyl.S-normalpropylthiophosphoric acid halide and substituted ethylmercaptoethylmercaptans. Said organo phosphoric acid dithioester has excellent insecticidal activity against a wide variety of insects.

3 Claims, No Drawings

PHOSPHORIC ACID DITHIOESTERS, AND INSECTICIDES CONTAINING SAID DITHIOESTERS

BACKGROUND OF THE INVENTION

The present invention relates to novel organo phosphoric acid dithioesters. More specifically this invention relates to novel organo phosphoric acid dithioesters which have excellent insecticidal activity against a wide variety of insect pests. This invention also relates to a process for the preparation of said dithioesters, and insecticides containing said dithioesters as an effective components. The term "insecticides" as used herein means both insecticides and miticides.

DESCRIPTION OF THE PRIOR ART

Various compounds have heretofore been known to be effective as insecticides. Organo phosphoric insecticides are among conventional insecticides, and as such organo phosphoric insecticides, compounds having the formulae shown below, for example, are disclosed as having insecticidal activity.

$$\begin{array}{c}C_2H_5O\\ \phantom{C_2H_5O}\diagdown\!\!\overset{S}{\underset{\|}{}}\\ \phantom{C_2H_5OOOO}P-OCH_2CH_2OCH_2CH_2SC_2H_5\\ \phantom{C_2H_5O}\diagup\\ C_2H_5O\end{array}$$

(Japanese Patent Publication No. 31-6349);

$$\begin{array}{c}C_2H_5O\\ \phantom{C_2H_5O}\diagdown\!\!\overset{S}{\underset{\|}{}}\\ \phantom{C_2H_5OOOO}P-SCH_2CH_2SCH_2SC_2H_5\\ \phantom{C_2H_5O}\diagup\\ C_2H_5O\end{array}$$

(Japanese Patent Publication No. 32-10479);

$$\begin{array}{c}C_2H_5O\\ \phantom{C_2H_5O}\diagdown\!\!\overset{O}{\underset{\|}{}}\\ \phantom{C_2H_5OOOO}P-SCH_2SCH_2SC_2H_5\\ \phantom{C_2H_5O}\diagup\\ C_2H_5O\end{array}$$

(Japanese Patent Publication No. 37-6850).

The effectiveness of the above substances, however, are not always sufficiently high.

Parathion was used to control insects of rice plants, tree fruits, vegetables and so forth. However, because of the great danger of parathion causing acute intoxication of mammals, its use is not prohibited by law in Japan.

Large amounts of various organo phosphoric, carbamic acid-based and pyrethroid-based insecticides have been used to kill or control insects. In recent years, however, an undesirable problem has arisen in that the insects acquire a resistance against the insecticides.

SUMMARY OF THE INVENTION

An object of the present invention is to provide novel insecticides which exhibit selective toxicity between mammals and insets, and which are effective in controlling insects having acquired resistance against conventional insecticides.

Another object of the present invention is to provide insecticides which meet the demand of the market and are more improved in effectiveness than the conventional insecticides.

The present invention relates to novel organo phosphoric acid dithioesters represented by the general formula (I):

$$\begin{array}{c}C_2H_5O\\ \phantom{C_2H_5O}\diagdown\!\!\overset{O}{\underset{\|}{}}\\ \phantom{C_2H_5OOOO}P-SCH_2CH_2SCH_2CH_2R\\ \phantom{C_2H_5O}\diagup\\ n\text{-}C_3H_7S\end{array}$$

(wherein R represents a lower alkylmercapto group, a thiophenyl group or a thiobenzyl group), to a process for preparing the above dithioesters, and to insecticides containing the above dithioesters as an effective component.

DETAILED DESCRIPTION OF THE INVENTION

The dithioesters of the present invention exhibit a high ability to specifically kill insects and mites, have excellent insecticidal activity, and furthermore are effective in killing or controlling a wide variety of insects, particularly mites which have developed a resistance against various organo phosphoric insecticides.

The dithioesters of the present invention further have advantages in that they do not damage plants, their insecticidal effect is of high reliability and in that they are satisfactory in both rapid insecticidal action and persistent insecticidal effect. Thus the dithioesters of the present invention can be used as useful agricultural chemicals to kill and control a wide variety of insects.

Insects to which the dithioesters of the present invention can be effectively applied include aphides such as *Myzus persicae, Aphis gossypii, Aphis craccivora, Aulacorthum solani,* and *Toxoptera citricidus,* curculios such as *Arthonomus grandis, Lissorhoptrus oryzophilus, Callosobruchus chinensis,* and *Rhyncrites heros,* insects belonging to the order of lepidoptera such as *Adoxophyes orana,* Adoxophyes sp., *Archips fuscocupreanus, Ostrinia furnacelis, Operophthera brumota,* and *Spodoptera litura,* and hemiptera such as *Nephotettix cincticeps, Laodelphax striatellus* and *Nilaparvata lugens.* In addition, the dithioesters of the present invention are effective in killing mites such as *Panonychus ulmi, Panonychus citri, Tetranychus urticae* and *Tetranychus cinnabarinus.*

The dithioesters of the present invention can be prepared by various methods. Their typical methods of preparation are described below.

Process (a):

O-ethyl.S-normalpropyldithiophosphoric acid salts represented by the general formula (II):

$$\left(\begin{array}{c}C_2H_5O\\ \phantom{C_2H_5O}\diagdown\!\!\diagup\!\!\overset{O}{}\\ \phantom{C_2H_5OOOO}P\\ \phantom{C_2H_5O}\diagup\!\!\diagdown\!\!\phantom{}_S\\ n\text{-}C_3H_7S\end{array}\right)M$$

(wherein M represents an alkali metal atom or an ammonium group) are reacted with substituted ethylmercaptoethyl halides represented by the general formula (III):

$$XCH_2CH_2SCH_2CH_2R$$

(wherein X represents a halogen atom, and R represents a lower alkylmercapto group, a thiophenyl group or a thiobenzyl group) to prepare the dithioesters of the present invention, i.e., the compounds of the general formula (I).

This reaction can be schematically illustrated as follows:

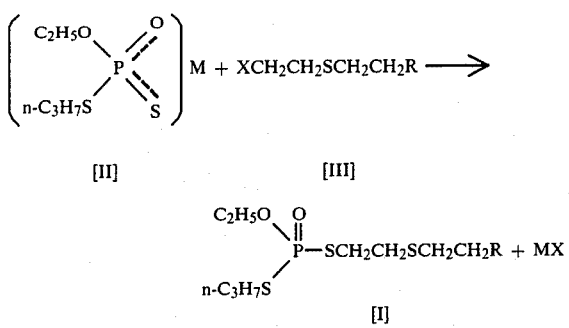

(wherein M, X and R are the same as defined above).

More specifically, in the general formulae (I), (II) and (III), M represents an alkali metal such as a potassium atom and a sodium atom, or an ammonium group. Preferably M is a sodium atom or a potassium atom. X represents a halogen atom such as a fluorine atom, a chlorine atom, a bromine atom or an iodine atom. Preferably X is a chlorine atom. R represents a methylmercapto group, an ethylmercapto group, a n-propylmercapto group, an iso-propylmercapto group, a n-butylmercapto group, an isobutylmercapto group, a sec-butylmercapto group, a thiophenyl group, a substituted thiophenyl group, a thiobenzyl group, a substituted thiobenzyl group or like groups.

The amount of the compound of the general formula (II) used is about 0.5 to 3 moles, preferably about 1 to 1.5 moles per mole of the compound of the general formula (III).

The above reaction is carried out in either an inert solvent or a diluent. Suitable examples of inert solvents and diluents which can be used in the present invention are water, alcohols such as methanol, ethanol, n-propanol, isopropanol, n-butanol and tert-butanol, ehers such as ethyl ether, dioxane and tetrahydrofuran, ketones such as acetone and methyl ethyl ketone, nitriles such as acetonitrile and propionitrile, amides such as dimethylformamide, dimethylacetamide and hexamethylphosphoric triamide, esters such as methyl acetate and ethyl acetate, aliphatic and aromatic hydrocarbons such as n-hexane, benzene, toluene and xylene, halogenated hydrocarbons such as methylene chloride, chloroform, carbon tetrachloride and chlorobenzene, and sulfoxides such as dimethyl sulfoxide.

The reaction temperature can be chosen appropriately from the range of about $-20°$ C. to $150°$ C. In general, the reaction is suitably carried out in the temperature range of about $0°$ C. to $100°$ C. The reaction can be carried out under pressure or under reduced pressure.

Although the exact reaction time varies with the type of R of the general formula (I), the reaction is usually completed in about 0.5 to 10 hours.

The end of the reaction can be confirmed by known techniques such as thin layer chromatography, high speed liquid chromatography and gas chromatography.

The dithioesters of the present invention of general formula (I) thus obtained can be isolated and purified by known isolation and purification techniques such as washing, solvent extraction, vacuum concentration, vacuum distillation and chromatography.

Process (b):

O-ethyl.S-normalpropylthiophosphoryl halides represented by the general formula (IV):

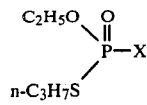

(wherein X represents a halogen atom) are reacted with substituted ethylmercaptoethylmercaptans represented by the general formula (V):

M'SCH$_2$CH$_2$SCH$_2$CH$_2$R (wherein M' represents a hydrogen atom or an alkali metal atom, and R represents a lower alkylmercapto group, a thiophenyl group or a thiobenzyl group) or their salts to prepare the dithioesters of the present invention.

This reaction can be schematically illustrated as follows:

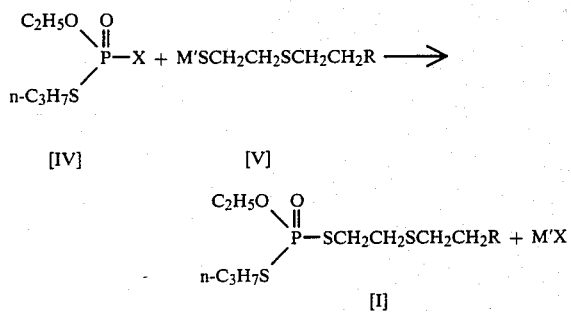

(wherein X, M' and R are the same as defined above).

More specifically, in the above general formula (I), (IV) and (V), X is the same as defined above and represents a halogen atom, such as a fluorine atom, a chlorine atom, a bromine atom and an iodine atom. Preferably X is a chlorine atom. M' represents a hydrogen atom or an alkali metal such as a potassium atom and a sodium atom. Preferably M' is a hydrogen atom or a sodium atom. R is the same as defined above and represents a methylmercapto group, an ethylmercapto group, a n-propylmercapto group, an iso-propylmercapto group, a n-butylmercapto group, an iso-butylmercapto group, a sec-butylmercapto group, a thiophenyl group, a substituted thiophenyl group, a thiobenzyl group, a substituted thiobenzyl group or like groups.

The amount of the compound of the general formula (V) used in the above reaction is about 0.5 to 3 moles, preferably about 1 to 1.5 moles per mole of the compound of the general formula (IV).

The reaction is carried out either in an inert solvent or a diluent. Suitable examples of inert solvents and diluents which are used in the present invention are aliphatic or aromatic hydrocarbons such as n-hexane, ligroin, petroleum ether, cyclohexane, benzene, toluene and xylene, halogenated hydrocarbons such as methylene chloride, chloroform, carbon tetrachloride, dichloroethane and chlorobenzene, alcohols such as methanol, ethanol, n-propanol, iso-propanol, n-butanol and tert-butanol, ketones such as acetone, methyl ethyl ketone and methyl isobutyl ketone, esters such as methyl acetate and ethyl acetate, ethers such as ethyl ether, dioxane and tetrahydrofuran, amides such as dimethylformamide, dimethylacetamide and hexamethylphosphoric triamide, and sulfoxides such as dimethylsulfoxide.

When M' of the general formula (V) is a hydrogen atom, the compound of the general formula (V) may be reacted directly with the compound of the genral formula (IV). It is preferred, however, that they be reacted in the presence of an acid acceptor.

Acid acceptors which can be used include aliphatic tertamines such as trimethylamine, triethylamine, tripropylamine and tributylamine, aromatic tert-amines such as dimethylaniline and diethylaniline, heterocyclic amines such as pyridine, α-picoline and γ-picoline, and inorganic bases such as sodium hydrogencarbonate, sodium carbonate and potassim carbonate.

The reaction temperature can be chosen appropriately from the range of about −20° C. to 150° C. In general, the reaction is suitably carried out in the temperature range of about 0° C. to 100° C. The reaction can be carried out under pressure or under reduced pressure.

Although the exact reaction time varies with the type of R of the general formula (I), the reaction is usually completed in about 0.5 to 10 hours.

The end of the reaction can be confirmed by known techniques such as thin layer chromatography, high speed liquid chromatography and gas chromatography.

The dithioesters of the present invention of general formula (I) thus obtained can be isolated and purified by known isolation and purification techniques such as washing, solvent extraction, vacuum concentration, vacuum distillation and chromatography.

The dithioesters of the present invention as prepared by the above methods, for example, have specific refractive indexes and, threfore, can be identified by measuring their refractive indexes.

Insecticides and/or miticides containing the dithioesters of the present invention as an effective component will be explained hereinafter.

In practice, the dithioesters of the present invention can be used as such depending on the proposed use. In general, however, to ensure or stabilize the effectiveness of the dithioesters of the present invention, adjuvants for pesticides are compounded to the dithioesters to prepare agricultural formulation, which are then applied as such or, if necessary, after being diluted.

Agricultural formulations containing the dithioesters of the present invention can be prepared in any desired form such as powders, granules, finely divided particles, wettable powders, flowables, microcapsules, oil solutions, aerosols, fumigants, smoking generators, poison baits, and so forth.

Adjuvants for pesticides which can be used include a carrier (diluent), and other auxiliary agents such as a spreader, an emulsifier, a wetting agent, a dispersing agent, a sticking agent and a disintegrating agent.

Suitable examples of the liquid carrier are aromatic hydrocarbons such as toluene and xylene, alcohols such as methanol, butanol and glycol, ketones such as acetone, amides such as dimethylformamide, sulfoxides such as dimethylsulfixide, methylnaphthalene, cyclohexene, animal and vegetable oil, fatty acid and fatty acid esters. In addition, oil fractions such as kerosene and gas oil can be used.

Suitable examples of the solid carrier are clay, kaoline, talc, diatomaceous earth, silica, calcium carbonate, montmorillonite, bentonite, feldspar, alumina and sawdust.

As emulsifiers or dispersing agents, surface active agents are usually used, including anionic, cationic, nonionic and amphoteric surface active agents, such as higher alcohol sulfuric acid sodium salts, stearyltrimethylammonium chloride, polyoxyethylene alkylphenyl ether and laurylbetaine.

Suitable examples of the spreader are polyoxyethylene nonylphenyl ether and polyoxyethylene lauryl ether. A suitable example of the wetting agent is polyoxyethylene nonylphenyl ether dialkylsulfosuccinate. Suitable examples of the sticking agent are carboxymethyl cellulose and polyvinyl alcohol. Suitable examples of the disintegrating agent are sodium ligninsulfonate and sodium laurylsulfate.

Mixtures comprising two or more of the dithioesters of the present invention can be used to enhance their ability to kill insects and mites. Other physiologically active substances other than the dithioesters of the present invention such as insecticides, miticides, fungicides, germicides, nematocides, herbicides, plant growth regulators, fertilizers, BT agents and insect hormones can be added to the dithioesters of the present invention to prepare excellent multi-purpose compositions. Furthermore, synergistic effects can be expected by compounding the above physiologically active substances to the dithioesters of the present invention.

The effective component content of the insecticide and miticides composition of the present invention varies with conditions such as form of application and application method. In some cases, only the dithioesters of the present invention as the effective component can h=applied. Usually the effective component content is about 0.2 to 95% by weight and preferably about 0.5 to 80% by weight.

Also, the amount of the insecticide composition of the present invention being used varies with conditions such as form of application, application method and application season. When used as an agricultural chemical, a forest insect-controlling agent or a pasture insect-controlling agent, the insecticide composition of the present invention is usually used in such an amount that the amount of the effective component applied per 10 ares is about 10 to 500 g and preferably 50 to 200 g. Of course, the present invention is not limited to the above specified ranges. In special cases, the insecticide composition of the present invention can be used or must be used in amounts exceeding the above upper limit or below the above lower limit.

The present invention is described in greater detail with reference to the following examples, although the present invention is not limited thereto.

EXAMPLE 1

Preparation of compound having the Formula:

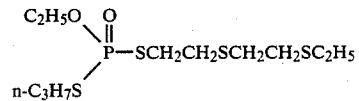

This compound is hereinafter referred to as "Compound 1".

26.2 g (0.11 mole) of potassium.O-ethyl.S-n-propylphosphorodithioate and 100 ml of methanol were mixed, and 18.5 g (0.1 mole) of β-ethylmercapto β'- chloroethyl thioether ether was dropped thereto with stirring at room temperature. After the dropwise addition, the mixture was reacted for 3 hours while refluxing the methanol. At the end of reaction time, the methanol was distilled away from the reaction mixture under reduced pressure. The residue was dissolved in a mixed solvent of 150 ml of toluene and 70 ml of water. After separation and removal of an aqueous layer, an organic layer was washed with a 4% aqueous solution of sodium bicarbonate and then with water. The toluene was distilled away under reduced pressure to yield 33.5 g of a light yellow oily substance (crude yield, 96.1%).

Upon purification of the above oily substance by column chromatography (silica gel: Wako Gel C-300 (trade name) manufactured by Wako Junyaku Kogyo Co., Ltd.; developing solvent: n-hexane/acetone (20/1 by volume)), 20.4 g of a colorless transparent oily substance, Compound 1, was obtained (yield, 58.6%). The refractive index ($nD^{25}$) of the oily substance was 1.5493.

EXAMPLE 2

Preparation of compound having the Formula:

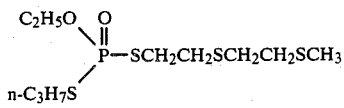

This compound is hereinafter referred to as "Compound 2".

16.8 g (0.1 mole) of 2'-methylmercapto-2-ethylmercaptoethylmercaptan (HS—CH$_2$CH$_2$SCH$_2$CH$_2$SCH$_3$), 10.6 g (0.105 mole) of triethylamine and 100 ml of toluene were mixied, and 20.3 g (0.1 mole) of O-ethyl.S-n-propylthiophosphoryl chloride was dropped thereto with stirring at room temperature. After the dropwise addition, the mixture was reacted at 40° C. for 3 hours. At the end of the reaction time, triethylamine hydrochloride by-produced was removed by filtration. A toluene layer was washed with a 5% aqueous solution of hydrochloric acid, with a 4% aqueous solution of sodium bicarbonate and then with water. The toluene was distilled away under reduced pressure to yield 31.1 g of a yellowish oily substance (crude yield, 93.0%).

Upon purification of the above oily substance by column chromatography (silica gel: Wako Gel C-300 (trade name) manufactured by Wako Junyaku Kogyo Co., Ltd.; developing solvent: n-hexane/acetone (20/1 by volume)), 22.2 g of a colorless transparent oily substance, Compound 2, was obtained (yield 66.4%). The refractive index ($nD^{25}$) of the oily substance was 1.5554.

EXAMPLE 3

Preparation of compound having the Formula:

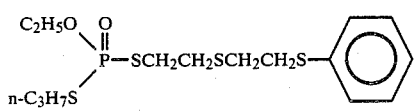

This compound is hereinafter referred to as "Compound 3".

26.2 g (0.11 mole) of potassium. O-ethyl.S-n-propyl-phosphoro dithioate and 100 ml of methanol were mixed, and 23.3 g (0.1 mole) of β-phenylmercapto β'-chloroethyl thioether was dropped thereto with stirring at room temperature. After the dropwise addition, the mixture was reacted at 50°–60° C. for 3 hours.

Then the methanol was distilled away from the reaction mixture under reduced pressure. The residue was dissolved in a mixed solvent of 150 ml of toluene and 70 ml of water. After separation and removal of an aqueous layer, an organic layer was washed with a 4% aqueous solution of sodium bicarbonate and then with water. The toluene was distilled away under reduced pressure to yield 38.7 g of a light brown oily substance (crude yield, 97.5%). Upon purification of the oily substance in the same manner as in Example 1, 19.2 g of a colorless transparent oily substance, Compound 3, was obtained (yield, 48.3%). The refractive index ($nD^{25}$) of the oily substance was 1.5867.

EXAMPLE 4

Preparation of compound having the Formula:

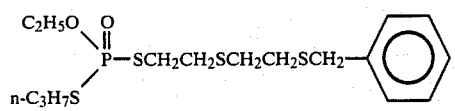

This compound is hereinafter referred to as "Compound 4".

26.2 g (0.11 mole) of potassium.O-ethyl.S-n-propyl-phosphorodithioate and 100 ml of methanol were mixed, and 24.7 g (0.1 mole) of β-benzylmercapto β'-chloroethyl thioether was dropped thereto with stirring at room temperature. After the dropwise addition, the mixture was reacted at 50°–60° C. for 3 hours. The methanol was distilled away under reduced pressure. The residue was dissolved in a mixed solvent of 150 ml of toluene and 70 ml of water. After separation and removal of an aqueous layer, an organic layer was washed with a 4% aqueous solution of sodium bicarbonate and then with water. The toluene was distilled away under reduced pressure to yield 40.6 g of a colorless transparent oily substance (crude yield, 99.0%).

Upon purification of the above oily substance in the same manner as in Example 1, 23.3 g of a colorless transparent oily substance, Compound 4, was obtained (yield, 56.8%). The refractive index ($nD^{25}$) of the oily substance was 1.5807.

EXAMPLE 5

Preparation of Emulsifiable Concentrate 20 parts by weight (hereinafter all parts are by weight) of Compound 1, 73 parts of xylene, 3 parts of polyoxyethylene alkylaryl ether, 2 parts of polyoxyethylene alkylphenol ether and 2 parts of an alkylallyl sulfonate metal salt were uniformly mixed to prepare an emulsifiable concentrate.

EXAMPLE 6

Preparation of Wettable Power 20 parts of Compound 2, 53 parts of clay, 20 parts of while carbon, 5 parts of lignin sulfonate and 2 parts of polyoxyethylene alkyl ether were mixed and finely powdered to prepare a wettable powder.

EXAMPLE 7

Preparation of Dust Formulation 5 parts of Compound 3 and 5 parts of white carbon were well mixed. Then 10 parts of clay was added to the above obtained mixture, which was then mixed and powdered. Additionally 80 parts of clay was added to the mixture to prepare a dust formulation.

EXAMPLE 8

Test of Insecticidal Activity against Carmine Spider Mite (*Tetranychus cinnabarinus*) (the Cup method)

A 3 cm×5 cm sections were cut out of kidneybeen leaves. These leaf sections were placed with their backs upward on a filter paper wetted with water. Then, the leaf sections were inoculated with carmine spider mite in such a manner that 10 female adults were present on the back of each section thereof. After one day, predetermined concentrations of chemicals prepared by diluting the emulsifiable concentrates of Compounds 1 to 4 prepared in the same manner as in Example 5 were sprayed on the leaf sections. The leaf sections were allowed to stand for one day in an incubator maintained at 26° C. Then, the insecticidal activity of each compound against the adults was determined. All adults, alive or dead, at the time of examination were removed, but eggs oviposited by the adults during the period from the inoculation to the examination were left as such. After 6 days, the eggs and the hatched larvae were examined for life or death.

The above test was repeated twice, and the mean values of the two tests are shown in Table 1.

TABLE 1

| Compound No. | Concentration of Effective Component (ppm) | Mortality of Adults (%) | Mortality of Eggs (%) | Mortality of Hatched Larvae (%) |
|---|---|---|---|---|
| 1 | 200 | 100 | 90 | 100 |
|   | 20  | 100 | 39 | 100 |
| 2 | 200 | 100 | 90 | 100 |
|   | 20  | 100 | 20 | 100 |
| 3 | 200 | 100 | 100 | — |
|   | 20  | 100 | 95 | 100 |
| 4 | 200 | 100 | 90 | 100 |
|   | 20  | 100 | 76 | 100 |

EXAMPLE 9

Test of insecticidal activity against Common Cutworm (*Spodoplera litura*)

Predetermined concentrations of chemicals prepared by diluting the wettable powder of Compounds 1 to 4 prepared in the same manner as in Example 6 were sprayed on Japanese radish leaves and then air dried. These leaves were placed in 21 cm long×13 cm wide×3 cm deep plastic containers, and then inoculated with 10 third-instar larvae of common cutworm. The containers were allowed to stand in the inculator at 26° C. After 24 hours, the numbers of dead and living larvae were counted.

The above test was repeated twice, and the mean values of the two tests are shown in Table 2.

EXAMPLE 10

Test of Insecticidal Activity Against Adoxophyes sp.

Predetermined concentrations of chemicals prepared by diluting the emulsifiable concentrate of Compounds 1 to 4 as prepared in the same manner as in Example 5 were sprayed on cucumber leaves and then air dried. The leaves were placed in 21 cm long, 13 cm wide×3 cm deep plastic containers, and then inoculated with 10 third-instar larvae of Adoxophyes sp. The containers were allowed to stand in the incubator at 26° C. After 24 hours after the inoculation, the numbers of dead and living larvae were counted.

The above test was repeated twice, and the mean values of the two tests are shown in Table 2.

EXAMPLE 11

Test of Insecticidal Activity against Green Rice Leafhopper (*Nephotettix cincticeps*)

Young rice plants having a plant length of about 7 cm were dipped in predetermined concentrations of chemicals prepared by diluting the wettable powder of Compounds 1 to 4 prepared in the same manner as in Example 6. After air drying, a sponge impregnated with water was wound on the roots of the young rice plants, which were then placed in plastic cylinders having a diameter of 11 cm and a height of 20 cm. 10 female adults of 3-5 days after emergence were introduced in the cylinders. The cylinders were allowed to stand in the incubator at 26° C. After 24 hours, the numbers of dead and liveing adults were counted.

The above test was repeated twice, and the mean values of two tests are shown in Table 2.

EXAMPLE 12

Test of Insecticidal Activity against Green Peach Aphids (*Myzus persical*)

Japanese radish leaves with green peach aphids harbored thereon were cut off and predetermined concentrations of chemical prepared by diluting the emulsions of Compounds 1 to 4 as prepared in the same manner as in Example 5 were sprayed on them. After air drying, the leaves were allowed to stand in the incubator at 26° C. After 24 hours, the numbers of dead and living adults were counted.

The above test was repeated twice, and the mean values of two tests are shown in Table 2.

TABLE 2

| Compound No. | Concentration of Effective Component (ppm) | Mortality of Adults (%) | | | |
|---|---|---|---|---|---|
| | | common cutworm | Adoxophyes sp. | green rice leafhopper | green peach aphid |
| 1 | 200 | 100 | 100 | 100 | 100 |
|   | 20  | 100 | 100 | 100 | 100 |
| 2 | 200 | 100 | 100 | 100 | 100 |
|   | 20  | 80  | 70  | 30  | 100 |
| 3 | 200 | 100 | 100 | 0   | 100 |
|   | 20  | 100 | 80  | —   | 100 |
| 4 | 200 | 100 | 100 | 0   | 100 |
|   | 20  | 11  | 0   | —   | 90  |

EXAMPLE 13

Test of Insecticidal Activity Against Rice Water Weevil (*Lissorhoptrus oryzophilus*) and White-backed Rice Planthopper (*Sogatella furcifera*)

Predetermined concentrations of chemicals prepared by diluting the emulsifiable concentrate of Compounds 1 and 2 as prepared in the same manner as in Example 5 were sprayed on young rice plants having a plant length of about 8 cm which had been grown in a 165 mm long×126 mm wide×51 mm deep plastic container. After air drying, the container was placed on the bottom of a 30 cm long×30 cm wide×25 cm deep stainless steel box the side walls of which were in a mesh form. 30 female adult rice water weevils and 30 female adult white-backed rice planthoppers were introduced in the box. This box was allowed to stand outdoors. After 48 hours, the numbers of dead and living adults were counted.

The above test was repeated twice, and the mean values of the two tests are shown in Table 3.

TABLE 3

| Type of Compound No. | Concentration of Effective Component (ppm) | Mortality of Adults (%) | |
| --- | --- | --- | --- |
| | | rice water weevil | white-backed rice planthopper |
| 1 | 200 | 100 | 100 |
| | 20 | 100 | 97 |
| 2 | 200 | 100 | 100 |
| | 20 | 90 | 87 |

The dithioesters of the present invention have advantages in that they cause no damage to plants, exhibit selective toxicity between warm blooded animals and insects, and further, as demonstrated in the foregoing examples, exhibit excellent insecticidal activity against a wide variety of insects. In particular, the dithioesters of the present invention exhibit high insecticidal activity against mites which have developed resistance to various organic phosphorcus insecticides.

The dithioesters of the present invention possess both rapid insecticidal action and persistent insecticidal effects which are important factors for agricultural chemicals, and are superior to conventional similar insecticides in the effect of killing insects and mites. Thus the dithioesters of the present invention are useful as agricultural chemicals; the present invention greatly contributes to increases in production of agricultural products.

What is claimed is:

1. An organo phosphoric acid dithioester represented by the general formula:

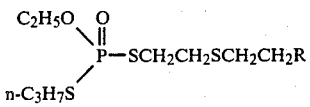

(wherein R represents a lower alkylmercapto group, a thiophenyl group or a thioebenzyl group).

2. An organo phosphoric acid dithioester according to claim 1, wherein R is a group selected from the group consisted of

3. An insecticide containing as an effective component an organo phosphoric acid dithioester represented by the general formula:

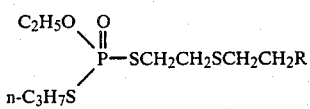

(wherein R represents a lower alkylmercapto group, a thiophenyl group or a thiobenzyl group).

* * * * *

UNITED STATES PATENT AND TRADEMARK OFFICE
CERTIFICATE OF CORRECTION

PATENT NO. : 4,694,095
DATED : Sept. 15, 1987
INVENTOR(S) : A. Kariya et al.

It is certified that error appears in the above-identified patent and that said Letters Patent is hereby corrected as shown below:

On the Title Page add: -- Foreign Application Priority Data
Aug. 13, [JP] Japan 60-176868

Column 11, line 27, "phosphorcus" should be -- phosphorous --.

Signed and Sealed this

Thirty-first Day of May, 1988

Attest:

DONALD J. QUIGG

Attesting Officer

Commissioner of Patents and Trademarks